United States Patent
Kersey et al.

(10) Patent No.: US 10,060,570 B2
(45) Date of Patent: Aug. 28, 2018

(54) SMART PIPE CONCEPT BASED ON EMBEDDED TAGGANT-SENSOR AND/OR COLOR-ENCODED ELEMENTS TO MONITOR LINER WEAR IN LINED PIPELINES, INCLUDING URETHANE LINED PIPE

(71) Applicant: CiDRA Corporate Services Inc., Wallingford, CT (US)

(72) Inventors: Alan D. Kersey, South Glastonbury, CT (US); Michael Puig, Wallingford, CT (US); Francis K. Didden, Wallingford, CT (US); Douglas H. Adamson, Mansfield Center, CT (US)

(73) Assignee: CiDRA CORPORATE SERVICES, INC., Wallingford, CT (US)

( * ) Notice: Subject to any disclaimer, the term of this patent is extended or adjusted under 35 U.S.C. 154(b) by 241 days.

(21) Appl. No.: 14/648,299

(22) PCT Filed: Jan. 9, 2014

(86) PCT No.: PCT/US2014/010888
§ 371 (c)(1),
(2) Date: May 29, 2015

(87) PCT Pub. No.: WO2014/110268
PCT Pub. Date: Jul. 17, 2014

(65) Prior Publication Data
US 2015/0345688 A1    Dec. 3, 2015

Related U.S. Application Data

(60) Provisional application No. 61/750,632, filed on Jan. 9, 2013, provisional application No. 61/873,958, filed on Sep. 5, 2013.

(51) Int. Cl.
*F16L 55/00* (2006.01)
*F16L 58/02* (2006.01)
(Continued)

(52) U.S. Cl.
CPC ............ *F16L 58/02* (2013.01); *B65G 53/523* (2013.01); *F16L 57/06* (2013.01); *F16L 58/1009* (2013.01);
(Continued)

(58) Field of Classification Search
CPC ....................................................... F16L 58/02
(Continued)

(56) References Cited

U.S. PATENT DOCUMENTS

| 4,779,453 A | 10/1988 | Hopenfeld |
| 5,187,542 A | 2/1993 | Madzsar |

(Continued)

FOREIGN PATENT DOCUMENTS

| WO | 9008915 | 8/1990 |
| WO | 0061472 | 10/2000 |

(Continued)

*Primary Examiner* — Nicholas J Weiss
*Assistant Examiner* — Michael J Melaragno
(74) *Attorney, Agent, or Firm* — Ware, Fressola, Maguire & Barber LLP (57) ABSTRACT

Apparatus, including a pipeline, featuring at least one pipe liner or coating configured to line or coat a pipe for receiving a process fluid flow, configured with at least one chemical taggant or tracer, and also configured to respond to the process fluid flow, and provide an indication about a degree of liner or coating wear or a location of wear in the pipe. The apparatus may also include the pipe having the at least one pipe liner or coating configured therein.

47 Claims, 7 Drawing Sheets

Smart Pipe Taggant-Sensor Monitoring Using
Chemical Taggant-Signaling Of Wear In Lined Pipes (51) Int. Cl.
*F16L 57/06* (2006.01)
*F17D 5/02* (2006.01)
*B65G 53/52* (2006.01)
*F16L 58/10* (2006.01)
*G01M 3/22* (2006.01)
*G01N 23/223* (2006.01)
*G01M 3/00* (2006.01)

(52) U.S. Cl.
CPC .............. *F17D 5/02* (2013.01); *G01M 3/22* (2013.01); *F16L 2201/30* (2013.01); *G01M 3/005* (2013.01); *G01N 23/223* (2013.01)

(58) Field of Classification Search
USPC .......................................................... 138/36
See application file for complete search history.

(56) References Cited

U.S. PATENT DOCUMENTS

| | | | |
|---|---|---|---|
| 5,228,478 A * | 7/1993 | Kleisle | B65G 53/523 116/208 |
| 5,551,484 A | 9/1996 | Charboneau | |
| 6,067,844 A * | 5/2000 | Westbrook | G01N 15/0826 73/38 |
| 6,386,237 B1 * | 5/2002 | Chevalier | F16L 11/12 116/208 |
| 6,498,991 B1 * | 12/2002 | Phelan | G01M 3/18 138/104 |
| 6,644,917 B2 | 11/2003 | Zhao et al. | |
| 7,052,737 B2 * | 5/2006 | Kool | G01K 11/06 374/E11.006 |
| 8,215,164 B1 | 7/2012 | Hussain et al. | |
| 8,273,320 B2 | 9/2012 | DiTommaso et al. | |
| 8,568,573 B2 | 10/2013 | Winkie et al. | |
| 8,701,714 B2 * | 4/2014 | Jansson | B32B 1/08 138/104 |
| 8,733,437 B2 * | 5/2014 | Ware | E21B 43/2406 166/246 |
| 9,267,874 B2 * | 2/2016 | Lorenz | G01N 17/00 |
| 2001/0036667 A1 | 11/2001 | Tayebi et al. | |
| 2002/0020527 A1 * | 2/2002 | Kilaas | B01D 39/1653 166/250.01 |
| 2002/0189697 A1 * | 12/2002 | Jarvenkyla | B29C 44/022 138/127 |
| 2003/0118440 A1 * | 6/2003 | Zhao | C23C 30/00 415/118 |
| 2004/0067360 A1 * | 4/2004 | Steenblik | G06K 19/06009 428/402 |
| 2004/0074644 A1 | 4/2004 | Kotlar et al. | |
| 2008/0133193 A1 | 6/2008 | Gdanski et al. | |
| 2008/0274028 A1 * | 11/2008 | Lin | B41M 3/144 423/263 |
| 2009/0087912 A1 | 4/2009 | Ramos et al. | |
| 2009/0146381 A1 * | 6/2009 | Herrera | E21B 17/1057 277/336 |
| 2009/0162632 A1 | 6/2009 | Kirby et al. | |
| 2010/0062251 A1 * | 3/2010 | Merchant | D01D 5/30 428/374 |
| 2010/0132944 A1 | 6/2010 | Li et al. | |
| 2010/0307745 A1 | 12/2010 | Lafitte et al. | |
| 2012/0099954 A1 | 4/2012 | Teichrob et al. | |
| 2014/0332218 A1 * | 11/2014 | Castrogiovanni | E21B 43/24 166/302 |
| 2015/0140228 A1 * | 5/2015 | Kersey | B05D 3/067 427/512 |
| 2015/0253164 A1 * | 9/2015 | Kersey | G01F 1/64 73/861.08 |
| 2015/0345688 A1 * | 12/2015 | Kersey | F16L 57/06 138/145 |
| 2015/0353817 A1 * | 12/2015 | Kersey | E21B 43/267 166/250.12 |
| 2016/0372263 A1 * | 12/2016 | Adamson | H01G 4/14 |
| 2017/0018326 A1 * | 1/2017 | Sotzing | B32B 27/12 |
| 2017/0080403 A1 * | 3/2017 | Rothman | B01J 20/261 |

FOREIGN PATENT DOCUMENTS

| | | |
|---|---|---|
| WO | 2008084140 | 7/2008 |
| WO | 2012162609 | 11/2012 |
| WO | 2012177144 | 12/2012 |
| WO | 2013158308 | 10/2013 |

* cited by examiner

*FIG. 1*: Background: Urethane Lined Pipes
(PRIOR ART)

Urethane Lined — Lined pipeline for reduced wear

Urethane Lined

FIG. 1b

"SMART-pipe" concept with embedded sensor elements to provide liner integrity assurance — Sensors provide position & wear indication via taggant release

FIG. 2

FIG. 3: Smart Pipe Taggant—Sensor Monitoring Using Chemical Taggant—Signaling Of Wear In Lined Pipes General Structure of A Double Ended Monomer

FIG. 6: Color-Encoded Wear-Monitoring for Urethane-Lined Pipe

FIG. 7: Color-Based Wear Monitoring Concept

FIG. 8b      FIG. 8a

FIG. 8: Urethane Color-Signaling of Wear in Lined Pipes

FIG. 9

SMART PIPE CONCEPT BASED ON EMBEDDED TAGGANT-SENSOR AND/OR COLOR-ENCODED ELEMENTS TO MONITOR LINER WEAR IN LINED PIPELINES, INCLUDING URETHANE LINED PIPE

CROSS-REFERENCE TO RELATED APPLICATIONS

This application corresponds to international patent application serial no. PCT/US2014/010888, filed 9 Jan. 2014, which claims benefit to provisional patent application Ser. No. 61/750,632, filed 9 Jan. 2013, and provisional patent application Ser. No. 61/873,958, filed 5 Sep. 2013, which is incorporated by reference in their entirety.

This application is related to PCT patent application serial no. PCT/US14/10662, filed 8 Jan. 2014, which claims benefit to provisional patent application Ser. No. 61/750, 101, filed 8 Jan. 2013, which is hereby incorporated by reference in its entirety.

BACKGROUND OF THE INVENTION

1. Field of Invention

The present invention relates to techniques for monitoring wear in a liner of a pipe; and more particularly relates to techniques for monitoring wear in a liner of a pipe using a chemical taggant of tracer that may be detected to determine an indication about a degree of liner or coating wear or a location of wear in the pipe.

2. Description of Related Art

Interior pipewall coatings have been developed for highly abrasive applications in industrial sectors to mitigate erosion of the pipewall. One example of this is in the Oil Sands industry, where the 'tailings' from a bitumen recovery process plant, which comprises mainly water and clay/sands, is pumped to a tailing pond, or a dewatering process facility. In such applications, standard carbon steel pipes can erode through the side wall in a matter of months, particularly in locations where there are bends in the pipeline.

Several types of pipe coating have been proposed to reduce this wear, including hard metal coatings such as Chromium, and polymeric based materials, such as urethane coatings. With urethane coatings, such as IRACORE, the pipe lifetime can be considerably increased—potentially to as much as 10 years. However, it would be desirable to be able to monitor the integrity of the pipewall coating, and the extent of wear of the urethane.

Figures 1, 1A:
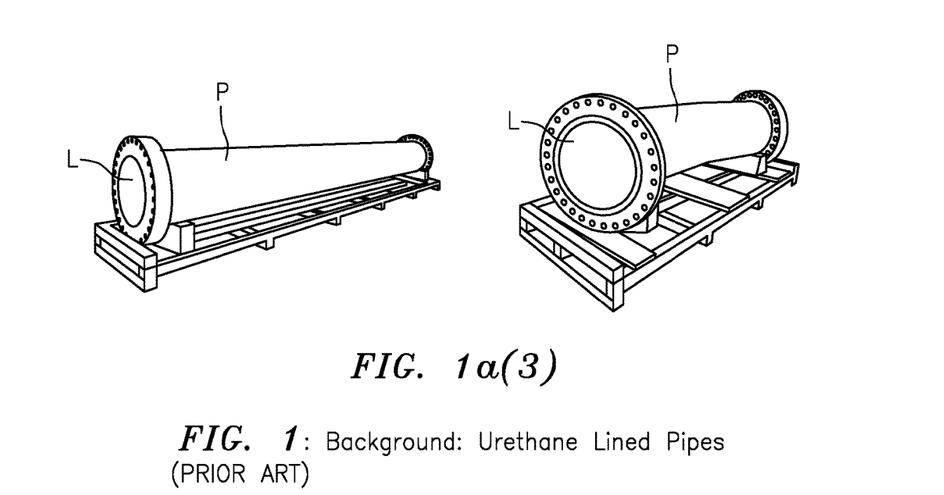
FIG. 1 includes FIGS. 1a(1), 1a(2), 1a(3) and 1b, where FIG. 1a(1) shows a piping system having known steel pipes, while FIG. 1a(2) shows one such steel pipe breached by highly abrasive fluid flowing therein; and where FIGS. 1a(3) and 1b show known pipes having Urethane pipe liner.
Figure 1A:
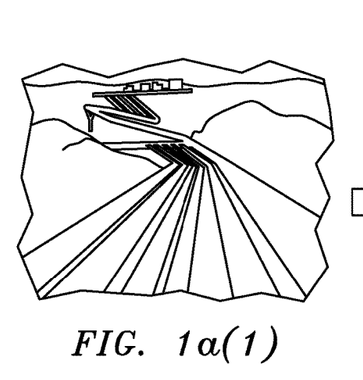

FIG. 1a(1) shows a piping system having known steel pipes, while FIG. 1a(2) shows one such steel pipe breached by highly abrasive fluid flowing therein.

Figure 1B:
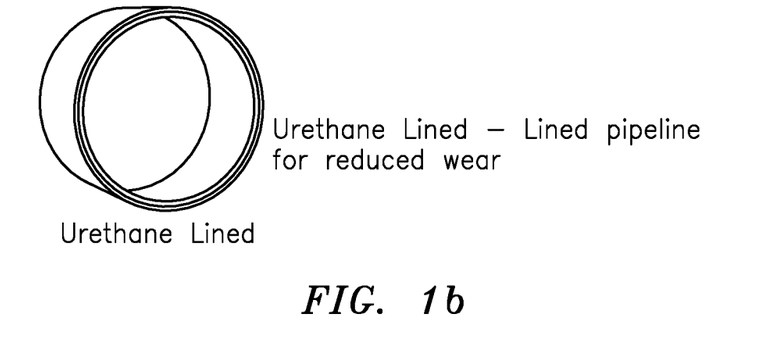

FIGS. 1a(3) and 1b show known pipes P having Urethane liner L.

In view of the aforementioned understanding, there is a need in the industry for a better way to monitor liner wear in pipelines.

SUMMARY OF THE INVENTION

The present invention provides a new and unique approach to monitoring the wear of a pipe liner or coating using embedded taggants that release chemical tracers into the flow to indicate the degree of liner or coating wear and location of wear in a pipeline.

The taggants could be incorporated as a core group or payload of a structure and could be a variety of chemical compounds, including, dyes, fluorescent molecules, nanoparticles, highly specific molecules such as perfluorocarbons, natural and or artificial DNA—such as Locked Nucleic Acid (LNA), which would provide the basis for a very large number of different taggants.

The taggants can be selected to indicate a variety of properties, such as the depth within the pipe liner, the circumferential position around the pipe liner and the linear position along the length of a section of pipe.

In addition to tailings applications in oil sands and hard rock mining, the monitoring system according to the present invention can be used for a variety of applications:

The embedded sensors/taggants could be directly incorporated into the liner matric material (e.g. immobilized within the polymeric structure), cross-linked into the matrix via ligands (chemical linkers), or incorporated into discrete beads and/or strips or other forms and embedded within the pipe lining, as well as a shell full of taggant or tracer material. The identifier (taggants) could be integrated into the coating polymer matrix using the above approaches at a certain layer depth (for example as the coating is applied on the inside of the pipe during manufacture, such as a coating that is applied by being spun, sprayed or cast onto the internal area of the pipe.

Each pipe section or spool can be identified by a specific tag or taggant. Additionally, by tagging the pipe with different identifiers at different layers or levels within the coating such as with a "sub-tag", the wear progression within specific sections or spools can be monitored.

The taggants can be selected to provide a high level of potential identifiers for a given pipeline. For example, by utilizing a type of synthetic DNA, potentially a very large number of identifiers or sequences will be available.

The aforementioned approach is based at least partly on incorporating taggants into urethanes used to line an internal wall of pipelines used in heavy slurry applications, such as those found in the Oil Sands industry.

Wear Detection Via Internal Inspection

Moreover, another new approach leverages the current form of pigments used to color the final cured urethane as a means of encoding the wear in the material when used to line the internal wall of a pipeline.

For example, with just 4 colors, a coating could be encoded in 4 locations for wear indication (e.g., a clear-to-colored transition with depth of wear); however, by using multiple combinations of pigments (e.g., with fractional amounts of each being added), many more 'color' variations become possible.

Color determination using current Red/Blue/Green (RBG) camera technology or 'hyperspectral imaging' technologies also allow these different colors to be determined.

It is important to note that this wear detection via international inspection concept is different from the aforementioned taggant concept, e.g., if the layers are color-coded, the wear may be assessed via an apparatus for conducting internal inspection of the pipe, in contrast to the concept of detecting or measuring a taggant or tracer in the flow stream.

In the taggant concept, different taggant can indicate wear at different locations along the pipe. In contrast, in the color coding concept, the same layers could be used along the entire pipe, and the apparatus for visualizing that color via the internal inspection may be configured to 'map out' the whole pipeline length.

In addition, the coating need not just be a color-based layer structure. By way of example, other approaches are envisioned, e.g., including embedding mineral elements into each layer, such as Zn, Cu, Mg, Ca, and detecting these embedded mineral elements, e.g., using an XRF instrument (mineral X-ray analyzer) over a color camera.

Examples of Particular Embodiments

Examples of particular embodiments of the present invention may include the following:

According to some embodiments, the present invention provides apparatus featuring at least one pipe liner or coating configured to line or coat a pipe for receiving a process fluid flow therein, configured with at least one chemical taggant or tracer, and also configured to respond to the process fluid flow, and provide an indication about a degree of liner or coating wear or a location of wear in the pipe, based at least partly on the at least one chemical taggant or tracer.

The apparatus may include, or take the form of, a pipe or pipeline configured with an inner pipewall surface to receive the at least one pipe liner or coating.

The present invention may also include one or more of the following features:

Embedded Sensors

The at least one pipe liner or coating may include at least one embedded sensor element configured from the at least one chemical taggant or tracer, e.g., configured as a functionalized polymer sensor or a sensor made from a functionalized polymer.

The functionalized polymer sensor may be configured or designed to respond to the process fluid flow and release a unique chemical taggant or tracer into the process fluid flow containing the indication when in contact with the process fluid, e.g., after part of the pipe liner or coating is worn away by an abrasive fluid and the functionalized polymer sensor is exposed to the fluid.

If the functionalized polymer sensor is embedded at a certain depth in the pipe liner or coating, then as wear of the pipe liner or coating increases, the functionalized polymer sensor will become exposed and release the at least chemical taggant or tracer.

The at least one chemical taggant or tracer may be made of a polymer, and fragments of the polymer are collected from a flow stream of the process fluid flow so as to indicate where the wear has reached a critical depth.

The apparatus may include a monitoring device or analyzer configured to monitor the flow stream at an output of the pipe, detect the at least one chemical taggant or tracer, and determine wear patterns in the pipe.

By way of example, and as one option, the functionalized polymer may include or take the form of a dual-monomer structure configured to allow the at least one chemical taggant or tracer to be incorporated as a payload/core group.

The payload/core group may be configured to incorporate the at least one chemical taggant or tracer.

The payload/core group may be configured as a chemical compound, including artificial DNA, e.g., including a Locked Nucleic Acid (LNA).

The at least one chemical taggant or tracer may include the Locked Nucleic Acid (LNA) or other Synthetic DNA (such as XNA) to create an identifier.

The at least one chemical taggant or tracer may be configured in the at least one pipe liner or coating to indicate properties selected from a group including: the depth within the pipe liner or coating, the circumferential position around the pipe liner or coating, and the liner position along the length of a section of pipe.

The process fluid flow may include tailings forming part of applications in oil sands and hard rock mining, or other abrasive industrial fluid.

The at least one embedded sensor element may include beads or strips located or configured within the pipe liner or coating.

The at least one the at least one chemical taggant or tracer may be directly incorporated into a coating polymer matrix applied to an internal surface of the pipe. For example, if the taggant or tracer is configured or incorporated into the polymer coating matrix, then it is understood that there is no 'definable" sensor element per se. In effect, the whole layer of coating with the taggants or tracer in it acts as a sensing layer. In contrast, if the taggant or tracer is encapsulated in the bead, or is incorporated into polymer beads, then there are more definable sensor elements. The scope of the invention is intended to include either configuration or implementation.

The coating polymer matrix may be configured to be applied at a certain layer depth, including where the coating is applied on the inside of the pipe during manufacture.

The at least one taggant sensor element may be embedded in the pipe liner or coating, so that each pipe section or spool can be identified by a specific tag.

The at least one taggant sensor element may be embedded in the pipe liner or coating, so that by tagging the pipe with different identifiers at different layers or levels within the pipe liner or coating, e.g., including with a "sub-tag", wear progression within specific sections or spools can be detected, determined and monitored, based at least partly on the at least one chemical taggant or tracer detected in the process flow.

The at least one chemical taggant or tracer may be configured and selected to provide a high level of potential identifiers for a given pipeline, including by utilizing a type of synthetic DNA, so that a large number of identifiers or sequences are available.

The scope of the invention is not intended to be limited to the type or kind of indication related to the release of the at least one chemical taggant or tracer, consistent with that set forth herein.

Color-Encoded Sensing

In summary, the concept of color coding is an approach to allow internal visual assessment or indication of wear. If a large number of color combinations—hues—are created, then the resolution of the detectable wear increases. By way of example, the concept may be configured with a plurality of colors, e.g., by using just 4 color and marking the 0-10-25%, 25-50%, 50-75% and 75-100% 'wear depth bands.

By way of example, when implementing such a concept the at least one pipe liner or coating may include at least one pigment.

The at least one pigment may include at least one material that provides a color, including, for example, yellow, red, blue and green.

The color is configured from mix formulations of each pigment.

By way of example, the mix formulations of each pigment may include:

formulations of about 0%, 33%, 66% or 100% of each so as to produce 256 combination of different colors; or formulations of about 0% or 100% of each so as to produce 16 combination of different colors.

The at least one pigment may form part of a colorimetric approach for a wear encoding.

The colorimetric approach may include each 'color' encoding a different pipe section for indicating that a critical depth had been reached.

A plurality of colors, e.g., such as four direct colors, or 16 different primary and composite colors, may be encoded into different depth layers of the pipe liner or coating applied to an inner wall of the pipe, including where each spray layer is given a different pigment combination, including where each layer is poured and set, sprayed or cast depending on the manufacturing process.

The mix formulations may form part of a colorimetric approach used to detect wear with a resolution via colorimetric observation of an internal coating surface of the pipe.

A pig or tractor may be configured to profile visually an entire pipeline having a pipe liner or coating according to the present invention. The pig or tractor may be configured to determine and use a pig or tractor position to provide position, and a pigment ratio encoding to provide a wear depth analysis.

The pipeline may also include or be configured with at least one beacon devices configured to provide external 'beacons' along the pipe, e. g., including an acoustic beacon, at at least one reference point for the pig or tractor to give an accurate position determination.

The pipe liner or coating may include modified pigment-loaded urethane coating layers, each modified pigment-loaded urethane coating layer configured with a different color.

Each modified pigment-loaded urethane coating layer may be configured to indicate a percentage of wear, including about 0-25%, 25-50%, 50-75% and 75-100%.

A first modified pigment-loaded urethane coating layer may be configured to indicate a percentage of wear, e.g., of about 50%.

The pig or tractor may be configured to assess the 'color' of an internal lining to map the wear along the entire pipeline.

The pig or tractor may be configured with some combination of a 'white light' source and color camera, a spectrometer, or hyperspectral type imager on-board with data collection and position tracking.

Mineral-Encoding Sensing

According to some embodiments of the present invention, the at least one pipe liner or coating may include or be configured with at least one identifiable compound, including at least one embedded mineral element, configured to provide the indication about the degree of liner or coating wear or the location of wear in the pipe. In effect, the liner or coating may be "encoded" to indicate its depth in both the color-based scheme and the mineral-based approach.

For example, identifiable compounds may be encoded into different depth layers of the pipe liner or coating applied to an inner wall of the pipe, including where each spray layer is given a different combination, and including where each layer is poured and set, sprayed or cast depending on the manufacturing process.

The identifiable compounds may include mix formulations of mineral elements that form part of an approach used to detect wear with a resolution via observation of an internal coating surface of the pipe, including using spectroscopic or analytical equipment and techniques.

The apparatus may include a pig or tractor configured to profile an entire pipeline, using a pig or tractor position to provide position, and a pigment ratio encoding to provide wear depth analysis.

The apparatus may also include at least one beacon devices configured to provide external 'beacons' along the pipe, including an acoustic beacon, as at least one reference point for the pig or tractor to give accurate position determination.

The pipe liner or coating may include modified mineral-loaded urethane coating layers, each modified mineral-loaded urethane coating layer configured with a different mineral.

Each modified mineral-loaded urethane coating layer may be configured to indicate a percentage of wear, including about 0-25%, 25-50%, 50-75% and 75-100%.

A first modified mineral-loaded urethane coating layer may be configured to indicate a percentage of wear.

The pig or tractor may be configured to assess the 'mineral' of an internal lining to map the wear along the entire pipeline.

The Method

According to some embodiments, the present invention may take the form of a method featuring steps for configuring a pipe with at least one pipe liner or coating to line or coat the pipe for receiving a process fluid flow, configuring the at least one pipe liner or coating with at least one chemical taggant or tracer, and also configuring the at least one pipe liner or coating to respond to the process fluid flow, and provide an indication about a degree of wear or a location of wear in the pipe.

The method may also include one or more of the features set forth herein.

Advantages

By way of example, some advantages of the present invention may include the following:

By monitoring the wear of the pipe liner or coating, the pipe can be replaced or repaired before rupturing, which can be a catastrophic and dangerous event in many industrial processes.

BRIEF DESCRIPTION OF THE DRAWING

The drawing includes FIGS. 1-9, which are not necessarily drawn to scale, as follows:

FIG. 6 includes FIGS. 6a and 6b, where

FIG. 8 includes FIGS. 8a and 8b, where FIG. 8a shows a pipe having a color-based wear monitoring liner, according to some embodiments of the present invention; and where FIG. 8b shows a piping system configured with one or more pipes having liners with Urethane color-signaling of wear, according to some embodiments of the present invention.

DETAILED DESCRIPTION OF BEST MODE OF THE INVENTION

FIGS. 2-5: Embedded Functionalized Sensor Techniques

Figure 2:
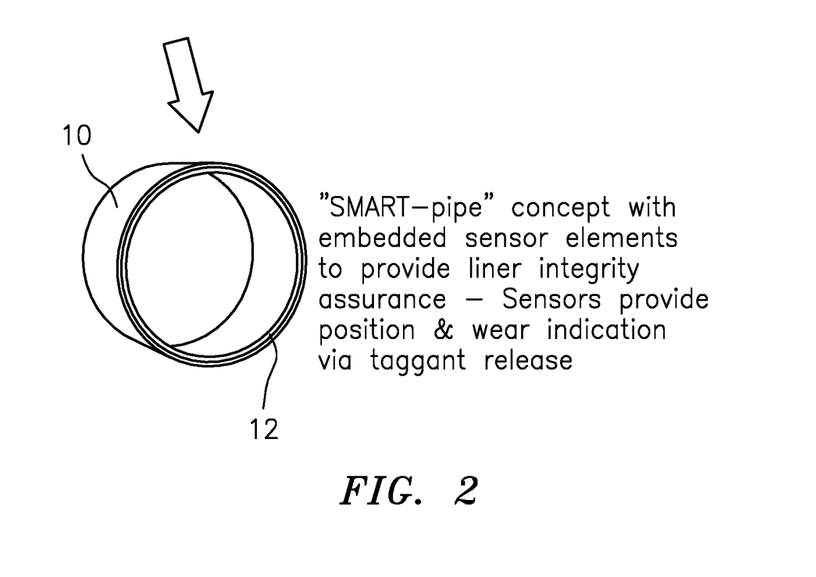
FIG. 2 shows generally a new lined pipe having embedded sensors, according to some embodiments of the present invention.

FIG. 2 shows a pipe 10 having a pipe liner or sensor-functionalized coating 12, according to some embodiments of the present invention. The pipe liner 12 has embedded sensor elements 14 to provide liner integrity assurance. The embedded sensor elements 14 can provide both position and wear indications via a taggant or tracer release.

The taggants or tracers are released by the embedded sensor 14 in the pipe liner 12 and are incorporated into the process fluid flow indicated by the term "FLOW." By way of example, taggant may be coded, e.g., to reveal 1) The position along the pipe 10; and
2) The wear condition of the pipe liner 12.

One embodiment of the present invention is to use 'embedded sensors' 14 based on a functionalized polymer sensors 14. These Functionalized Polymer Sensor (FPSs) 14 are configured or designed to release a unique chemical taggant or tracer when in contact with the process fluid in the flow.

Figure 3:
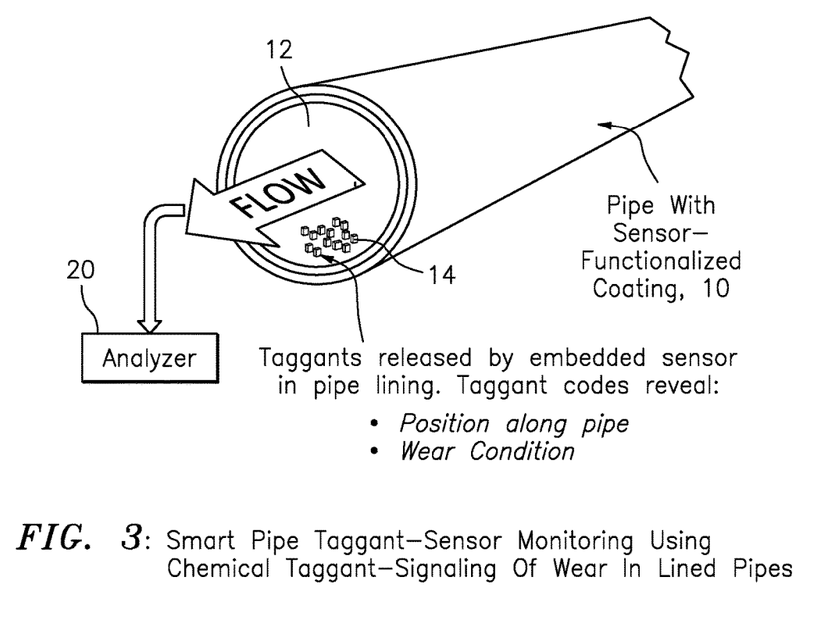
FIG. 3 shows a new lined pipe having embedded sensors that may be configured to form part of the prior art piping system shown in FIG. 1a(1), according to some embodiments of the present invention.

If the FPS elements 14 are embedded at a certain depth in the pipe liner or coating 12, then as the wear increases, the FPS elements 14 will become exposed and release their specific taggant or tracer. By monitoring the fluid stream at the output of the pipe 10, the various chemical tracers can be detected, and the wear patterns in the pipe liner or coating 12 determined. FIG. 3 shows an analyzer 20 that may be configured at the output of the pipe 10 for monitoring the process fluid flow.

Figure 4:
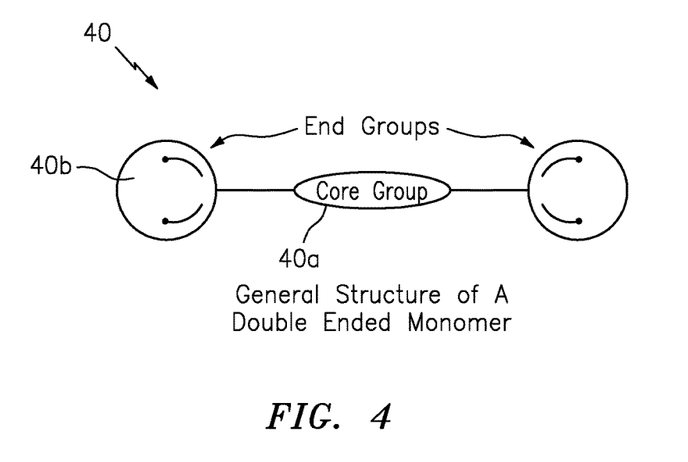
FIG. 4 shows an example of a functionalized polymer sensor configured from, or in the form of, a dual-monomer structure with a core group and end groups, according to some embodiments of the present invention.

By way of example, taggants or tracers may be incorporated as a core group or payload 40a of a dual-monomer structure 40 as shown in FIG. 4, and also can be implemented from a variety of other chemical compounds, including artificial DNA—known as Locked Nucleic Acid (LNA), which would provide the basis for a very large number of different taggants.

The taggants can be selected to indicate a variety of properties, such as the depth within the pipe liner 12, the circumferential position around the pipe liner 12 and the linear position along the length of a section of pipe 10.

In addition to tailings applications in oil sands and hard rock mining, the monitoring system of the present invention can be used for a variety of applications:

The taggant can be a Locked Nucleic Acid (LNA) or other Synthetic DNA (such as XNA) to create the identifier.

The embedded sensors/taggants could be beads and/or strips or other forms located within the pipe lining or coating 12. Alternatively, an identifier could be integrated into the coating polymer matrix at a certain layer depth (for example, as the coating is applied on the inside of the pipe during manufacture, such as a coating that is applied by being spun onto the internal area of the pipe 10.

Each pipe section or spool can be identified by a specific tag. Additionally, by tagging the pipe liner 12 with different identifiers at different layers or levels within the coating such as with a "sub-tag", the wear progression within specific sections or spools can be monitored.

The taggants can be selected to provide a high level of potential identifiers for a given pipeline. For example, by utilizing a type of synthetic DNA, potentially a very large number of identifiers or sequences will be available.

In summary, the scope of the invention is intended to include the chemical taggants or tracers being:

1. Directly incorporated into a polymer (in this case Urethane) and these are either released into the flow stream (leached), or as the polymer is worn away, release in polymer fragments; or 2. Contained in a "carriers"—beads, or other elements that get embedded into the coating (these act as 'carriers' of the taggants), consistent with that set forth herein.

FIG. 4: The Dual-Monomer Structure 40

As would be appreciated by a person skilled in the art, polymer formulations presently exist, are known in the art and well documented that allow the physical and chemical properties of a polymer substrate to be altered and controllable via an external influence. By way of example, the functionalized or functionizable polymer may take the form of a dual-monomer structure 40 that allows the tracer to be incorporated as a payload/core group, including where the dual-monomer structure like element 40 includes a core group 40a and end groups 40b, consistent with that shown in FIG. 4. Furthermore, the scope of the invention is not intended to be limited to any particular type or kind of polymer structure either now known or later developed in the future; and embodiments are envisioned with the scope of the present invention using other types or kinds of polymer structures and or functionalized polymers in addition to that disclosed herein by way of example.

Figure 5:
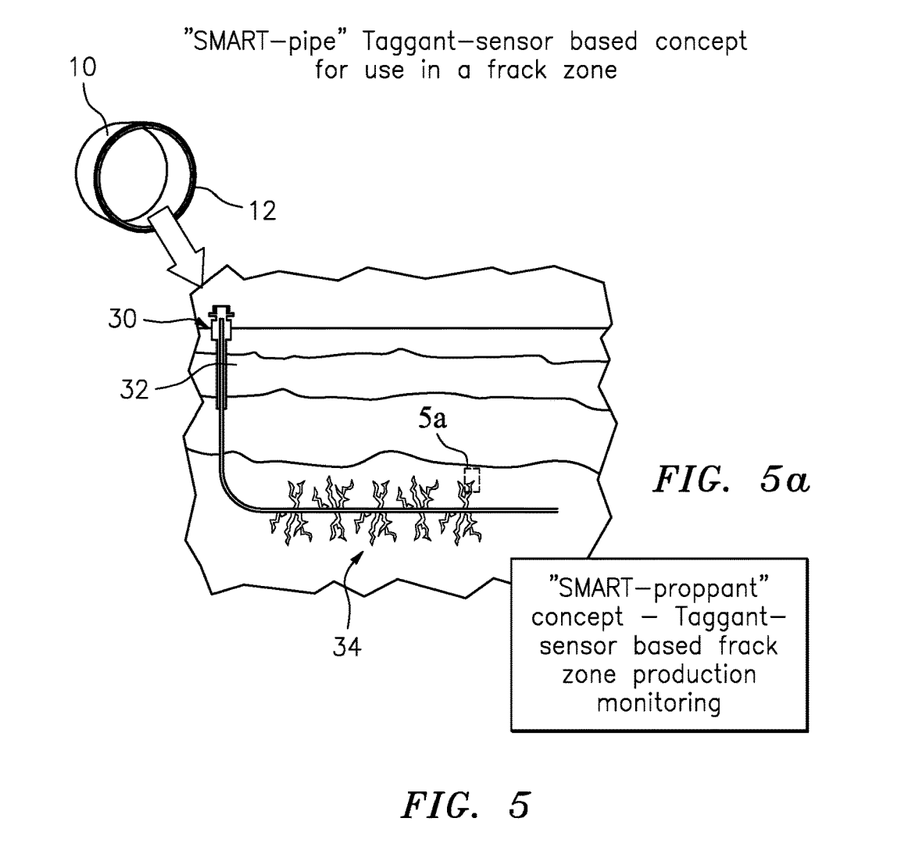
FIG. 5 shows an example of a well having piping that may be configured according to the present invention.

FIG. 5

FIG. 5 shows a new lined pipe 10 having a pipe liner or coating 12 that may be configured according to the present invention so as to form part of a well 30 having a borehole pipeline 32 and a fracking zone generally indicated as 34.

Figure 5A:
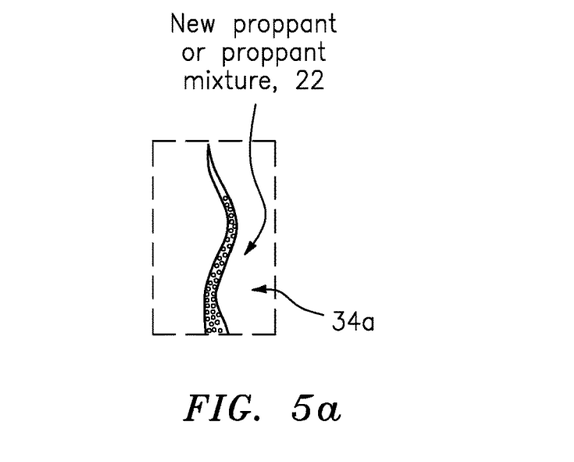

FIG. 5a shows an exploded view of one particular fracture or fissure generally indicated as 34a that forms part of the fracking zone 34 shown in FIG. 5 and contains a new proppant or proppant mixture generally indicated as 22, which includes functionalized polymer proppants, consistent with that disclosed in patent application serial no. PCT/US14/10662 (712-2.397-1//CCS-0113), filed 8 Jan. 2014. By way of example, the functionalized polymer proppants 22 may be configured or implemented, based at least partly on using the polymer technology disclosed herein and consistent with that described in further detail in the aforementioned patent application.

Figure 6A:
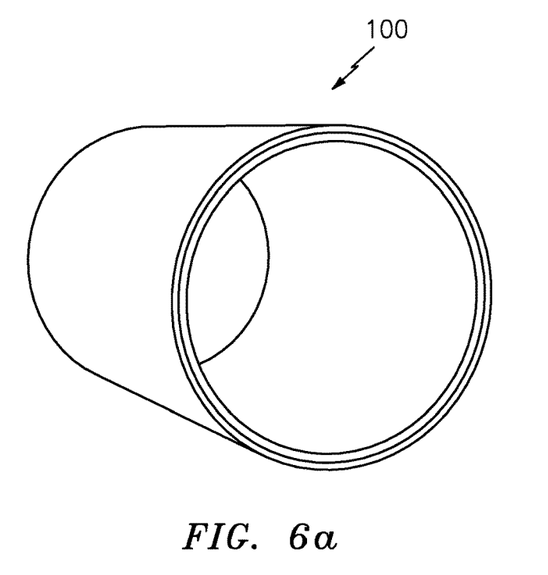
FIG. 6a shows a pipe having a new color-encoded wear-monitoring liner, according to some embodiments of the present invention, and where
Figure 6B:
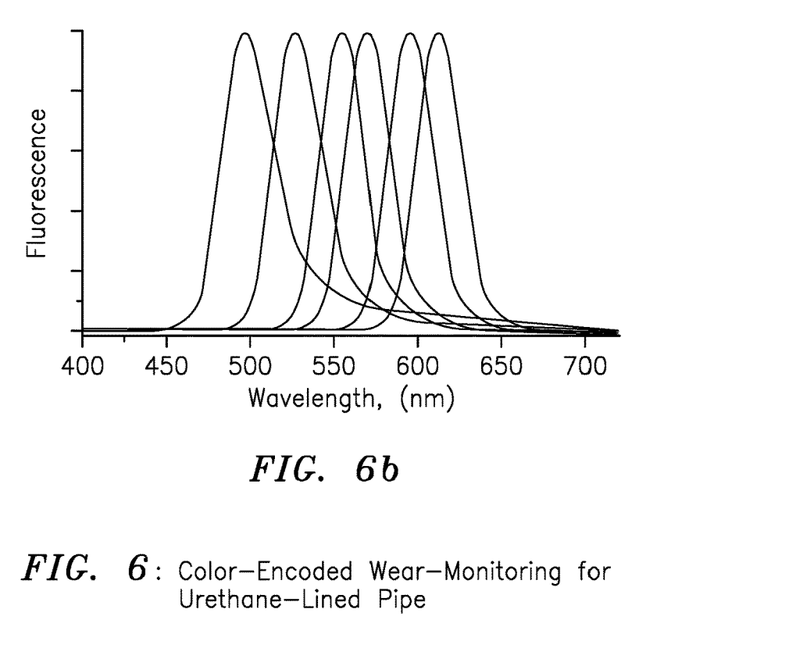
FIG. 6b shows graph of fluorescence versus wavelength (nm) for six different pigment colors (including from left to right turquoise, green, lime green, yellow, orange, red).
Figure 7:
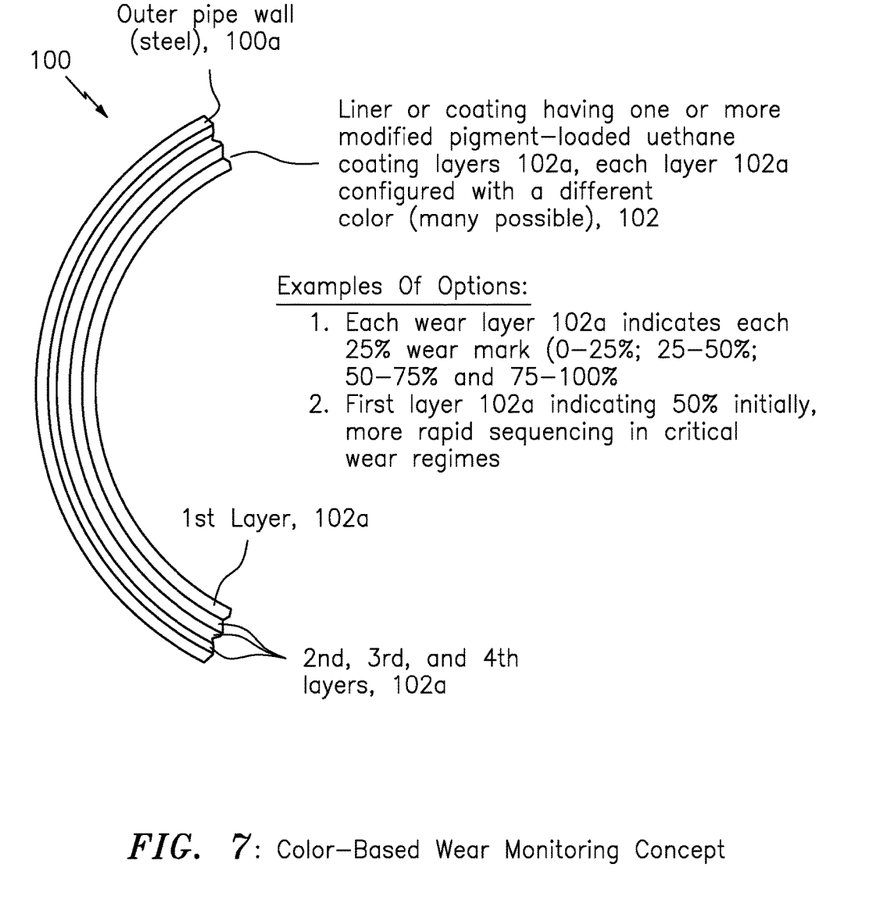
FIG. 7 shows a pipe having a color-based wear monitoring liner, according to some embodiments of the present invention.
Figures 8, 8A, 8B:
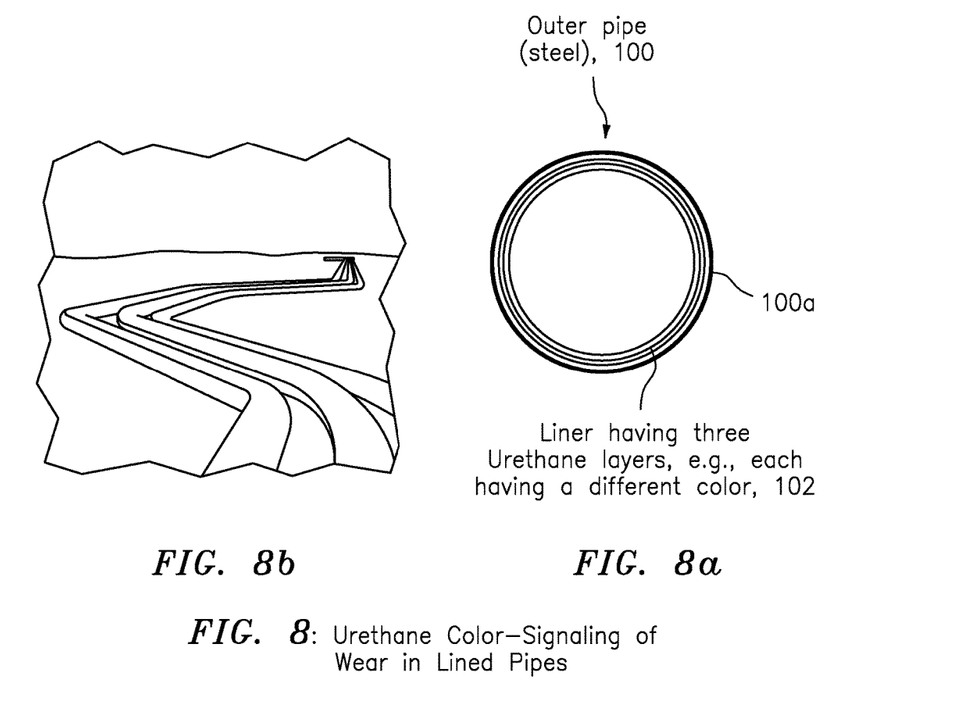

FIGS. 6-8: Color-Encoding Techniques

The aforementioned approach described in relation to FIGS. 2-5 is based at least partly on incorporating taggants or tracer into urethanes used to line an internal wall of a pipeline, e.g., that may be used in heavy slurry applications, such as those found in the Oil Sands industry In addition to that set forth above, another new approach is provided that leverages the current form of pigments used to color a final cured urethane as a means of encoding the wear in the material when used to line or coat the internal wall of a pipeline. FIGS. 6a, 7 and 8a show examples of a pipe 100 having such a color encoded pipe liner or coding 102.

By way of example, by using just 4 colors, the pipe liner or coating 102 may be encoded in 4 locations for providing wear indication (e.g., using a color scheme ranging from clear-to-colored transition with depth of wear); however, by using multiple combinations of pigments (e.g., with fractional amounts of each pigment being added), many more 'color' variations become possible, consistent with the present invention.

Moreover, color determination using known Red/Blue/Green (RBG) camera technology or 'hyperspectral imaging' technologies will allow these different colors to be determined.

Chemical Taggant-Signaling of Wear in Lined Pipes

FIGS. 6a, 7 and 8a show examples of the pipe 100 having the new color-encoded wear-monitoring liner or coating 102 having one or more layers. In FIG. 6a, the pipe 100 is shown with one layer (indicated in white); in FIG. 7, the pipe 100 is shown with four layers 102a (indicated as 1st, 2nd, 3rd and 4th); and in FIG. 8a, the pipe 100 is shown with three layers.

By way of example, the at least one chemical taggant or tracer may include, or take the form of, 4 pigments—e.g., Yellow, Red, Blue and Green, although the scope of the invention is not intended to be limited to any particular colors, or any particular combination of colors.

By way of further example, the pigments may be configured in or using mix formulations, e.g., of 0%, 33%, 66% or 100% of each pigment. Such a mix formulation will produces 256 combination of different colors. Many more combination are possible if finer ratios are used (e.g. TV panels use the same concept for 1000s of colors).

This colorimetric approach can be used as a wear encoding approach, e.g., with each 'color' encoding a different pipe section (e.g., indicating that a critical depth had been reached).

By way of example, fragments of polymer collected from the flow stream would indicate where the wear has reached critical depths.

Alternatively, the 4 pigments—e.g., Yellow, Red, Blue & Green, may be configured with mix formulations of just 0% or 100% of each, which produces 16 combination of different colors These 4 direct, or 16 different composite colors, may be encoded into different depth layers of the liner or coating 102 applied to the inner wall 100a of the pipe 100 (e.g., each spray layer may be given a different pigment combination).

This colorimetric approach can be used to detect wear with a reasonably high resolution via colorimetric observation of the internal coating surface of the pipe 100.

A pig or tractor 45 (FIG. 9) could be used to profile the entire pipe line, e.g., using the pig/tractor position to provide the position along the pipeline, and the pigment ratio encoding to provide a wear depth analysis. In operation, the 'pig' or tractor may be deployed to move along the pipeline during a scheduled shutdown to assess the 'color' of the internal lining to map the wear along the pipeline. The pig or tractor 45 (FIG. 9) may be configured to have a 'white light" source and color camera, a spectrometer, or hyperspectral type imager on-board with data collection and position tracking.

Figure 9:
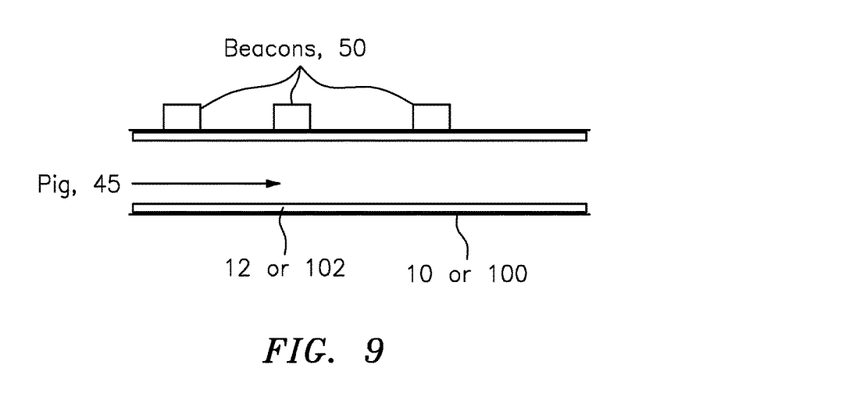
FIG. 9 shows a pipe or pipeline having the pipe liner or coating, according to the present invention, and also configured with external 'beacons' and a pig or tractor configured to traverse the inside of the pipe.

External 'beacons' 50 may be configured along the pipe 100 (e.g. acoustic) to provide reference points for the pig/tractor to give accurate position determination.

A Generic Liner or Coating Wear "Indicator" Approach

It is important to note that the scope of the invention is intended to include using a generic liner or coating wear "indicator" approach, and is not intended to be limited to the specific examples provided herein that are based at least partly the use of pigments (dyes) or minerals, consistent with that set forth by way of example herein. For example, while the liner or coating may be 'encoded' with pigments (dyes) or these mineral compounds to indicate different layers, e.g., through an XFR or Raman-based analysis, the scope of the invention is intended to include, and embodiments of the invention are envisioned in which this could be done, using many other types or kinds of materials or substances either now known or later developed in the future as so-called liner or coating wear "indicators". In such cases, the other types or kinds of materials or substances that could be used so-called liner or coating wear 'indicators' could be detected using other type or kinds of analytical approaches either now known or later developed in the future, as a person skilled in the would appreciate.

Using Bead as Functionalized Polymer Sensors

By way of example, functionalized polymer sensors may take the form of beads that may be configured as solid materials or capsules, e.g., either made from the functionalized polymer, or made or manufactured substantially using a shell of inert polymeric material (or other shell—e.g., ceramic) and filled with the taggant material. The bead may take the form of different geometric shapes, including at least partially spherical, partially tubular, etc.; and the scope of the invention is not intended to be limited to any particular type or kind of geometrical shape or dimension. By way of example, the bead may be hollow throughout, like a hollow tube; may be partially hollowed out, e.g., with an indent or recess; or may be solid in form, like a solid sphere or solid tubular structure or rod. By way of example, the reader is referred to PCT application no. PCT/US12/39576 (WFMB file no. 712-2.382), filed 25 May 2012, as well as the family of corresponding application disclosed and referred to therein, for examples of different geometric bead shapes and configurations.

By way of further example, the functionalized polymer may be formed in whole or in part on the surface of the bead; and the scope of the invention is not intended to be limited to the amount of surface that is covered with the functionalized polymer, the thickness of the layer of the functionalized polymer, etc.

Applications

By way of example, the present invention may be used in, or form part of, or used in conjunction with, industrial processes for processing flows, e.g., in oil/sands, etc.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
a pipe configured to receive a process fluid flow; and
at least one pipe liner or coating configured to line or coat the pipe, configured with at least one chemical taggant or tracer, and configured to respond to the process fluid flow, and provide an indication about a degree of liner or coating wear or a location of wear in the pipe, based at least partly on the at least one chemical taggant or tracer;
wherein the at least one pipe liner or coating comprises at least one embedded sensor element configured from the at least one chemical taggant or tracer and formed from a functionalized polymer, and
wherein the at least one embedded sensor element is embedded in the pipe liner or coating, so that by tagging the pipe with different identifiers at different layers or levels within the pipe liner or coating, including with a "sub-tag", wear progression within specific sections or spools can be detected, determined and monitored, based at least partly on the at least one chemical taggant or tracer detected in the process flow.

2. Apparatus according to claim 1, wherein the at least one embedded sensor element takes the form of either a functionalized polymer sensor or a sensor made from the functionalized polymer.

3. Apparatus according to claim 2, wherein the functionalized polymer sensor is configured or designed to respond to the process fluid flow and release a unique chemical taggant or tracer into the process fluid flow containing the indication when in contact with the process fluid flow.

4. Apparatus according to claim 2, wherein, if the functionalized polymer sensor is embedded at a certain depth in the pipe liner or coating, then as wear of the pipe liner or coating increases, the functionalized polymer sensor will become exposed and release the at least chemical taggant or tracer.

5. Apparatus according to claim 1, wherein the at least one chemical taggant or tracer is made of a polymer, and fragments of the polymer are collected from a flow stream of the process fluid flow so as to indicate where the wear has reached a critical depth.

6. Apparatus according to claim 1, wherein the apparatus comprises a monitoring device or analyzer configured to monitor the flow stream at an output of the pipe, detect the at least one chemical taggant or tracer, and determine wear patterns in the pipe.

7. Apparatus according to claim 2, wherein the functionalized polymer comprises a dual-monomer structure configured to allow the at least one chemical taggant or tracer to be incorporated as a payload/core group.

8. Apparatus according to claim 7, wherein the payload/core group is configured to incorporate the at least one chemical taggants or tracer.

9. Apparatus according to claim 8, wherein the payload/core group is configured as a chemical compound, including artificial DNA, also known as Locked Nucleic Acid (LNA), or could be a variety of chemical compounds, including, dyes, fluorescent molecules, nanoparticles, highly specific molecules such as perfluorocarbons.

10. Apparatus according to claim 1, wherein the at least one chemical taggant or tracer is configured in the at least one pipe liner or coating to indicate properties, selected from a group including the depth within the pipe liner or coating, the circumferential position around the pipe liner or coating, and the linear position along the length of a section of pipe.

11. Apparatus according to claim 1, wherein the process fluid flow includes tailings forming part of applications in oil sands and hard rock mining.

12. Apparatus according to claim 1, wherein the at least one chemical taggant or tracer comprises a Locked Nucleic Acid (LNA) or other Synthetic DNA (such as XNA) to create an identifier.

13. Apparatus according to claim 1, wherein the at least one embedded sensor element comprises beads or strips located within the pipe liner or coating.

14. Apparatus according to claim 1, wherein the at least one taggant sensor element comprises, or forms part of, a coating polymer matrix applied to an internal surface of the pipe.

15. Apparatus according to claim 14, wherein the coating polymer matrix is configured to be applied at a certain layer depth, including where the coating is applied on the inside of the pipe during manufacture.

16. Apparatus according to claim 1, wherein the at least one embedded sensor element is embedded in the pipe liner or coating, so that each pipe section or spool can be identified by a specific tag.

17. Apparatus according to claim 1, wherein the at least one chemical taggant or tracer is configured and selected to provide a high level of potential identifiers for a given pipeline, including by utilizing a synthetic DNA, so that a large number of identifiers or sequences are available.

18. Apparatus according to claim 1, wherein the at least one pipe liner or coating comprises at least one pigment.

19. Apparatus according to claim 18, wherein the at least one pigment comprises at least one material that provides color, including yellow, red, blue and green.

20. Apparatus according to claim 19, wherein the color is configured from mix formulations of each pigment.

21. Apparatus according to claim 20, wherein the mix formulations of each color includes:
formulations of about 0%, 33%, 66% or 100% of each so as to produce 256 combination of different colors; or
formulations of about 0% or 100% of each so as to produce 16 combination of different colors.

22. Apparatus according to claim 18, wherein the at least one pigment forms part of a colorimetric approach for a wear encoding.

23. Apparatus according to claim 22, wherein the colorimetric approach includes each 'color' encoding a different pipe section for indicating that a critical depth had been reached.

24. Apparatus according to claim 18, wherein the at least one pigment is made of a polymer, and fragments of the polymer are collected from a flow stream of the process fluid flow so as to indicate where the wear has reached a critical depth.

25. Apparatus according to claim 24, wherein the apparatus comprises a pigment detection device configured to collect the fragments of the polymer from the flow stream of the process fluid flow and determine where the wear has reached the critical depth.

26. Apparatus according to claim 21, wherein a plurality of colors, including primary or composite colors, are encoded into different depth layers of the pipe liner or coating applied to an inner wall of the pipe, including where each layer is given a different pigment combination, including where each layer is poured and set, sprayed or cast depending on the manufacturing process.

27. Apparatus according to claim 21, wherein the mix formulations form part of a colorimetric approach used to detect wear with a resolution via colorimetric observation of an internal coating surface of the pipe.

28. Apparatus comprising:
a pipe configured to receive a process fluid flow; and
at least one pipe liner or coating configured to line or coat the pipe, configured with at least one chemical taggant or tracer, and configured to respond to the process fluid flow, and provide an indication about a degree of liner or coating wear or a location of wear in the pipe, based at least partly on the at least one chemical taggant or tracer,
wherein the at least one pipe liner or coating comprises at least one pigment;
wherein the at least one pigment comprises at least one material that provides color, including yellow, red, blue and green;
wherein the color is configured from mix formulations of each pigment;
wherein the mix formulations of each color includes:
formulations of about 0%, 33%, 66% or 100% of each so as to produce 256 combination of different colors; or
formulations of about 0% or 100% of each so as to produce 16 combination of different colors;
wherein the mix formulations form part of a colorimetric approach used to detect wear with a resolution via colorimetric observation of an internal coating surface of the pipe; and
wherein the apparatus comprises a pig or tractor configured to profile an entire pipeline, using a pig or tractor position to provide position, and a pigment ratio encoding to provide wear depth analysis.

29. Apparatus according to claim 28, wherein the apparatus comprises at least one beacon devices configured to provide external 'beacons' along the pipe, including an acoustic beacon, as at least one reference point for the pig or tractor to give accurate position determination.

30. Apparatus comprising:
a pipe configured to receive a process fluid flow; and
at least one pipe liner or coating configured to line or coat the pipe, configured with at least one chemical taggant or tracer, and configured to respond to the process fluid flow, and provide an indication about a degree of liner or coating wear or a location of wear in the pipe, based at least partly on the at least one chemical taggant or tracer,
wherein the at least one pipe liner or coating comprises at least one pigment; and
wherein the pipe liner or coating comprises modified pigment-loaded urethane coating layers, each modified pigment-loaded urethane coating layer configured with a different color.

31. Apparatus according to claim 30, wherein each modified pigment-loaded urethane coating layer is configured to indicate a percentage of wear, including about 0-25%, 25-50%, 50-75% and 75-100%.

32. Apparatus according to claim 30, wherein a first modified pigment-loaded urethane coating layer is configured to indicate a percentage of wear.

33. Apparatus according to claim 28, wherein the pig or tractor is configured to assess the 'color' of an internal lining to map the wear along the entire pipeline.

34. Apparatus according to claim 28, wherein the pig or tractor is configured with some combination of a 'white light source and color camera, a spectrometer, or hyperspectral type imager on-board with data collection and position tracking.

35. Apparatus according to claim 1, wherein the at least one pipe liner or coating comprises at least one identifiable compound, including at least one embedded mineral element, configured to provide the indication about the degree of liner or coating wear or the location of wear in the pipe.

36. Apparatus according to claim 35, wherein identifiable compounds are encoded into different depth layers of the pipe liner or coating applied to an inner wall of the pipe, including where each layer is given a different combination, and including where each layer is poured and set, sprayed or cast depending on the manufacturing process.

37. Apparatus comprising:
a pipe configured to receive a process fluid flow; and
at least one pipe liner or coating configured to line or coat the pipe, configured with at least one chemical taggant or tracer, and configured to respond to the process fluid flow, and provide an indication about a degree of liner or coating wear or a location of wear in the pipe, based at least partly on the at least one chemical taggant or tracer,
wherein the at least one pipe liner or coating comprises at least one identifiable compound, including at least one embedded mineral element, configured to provide the indication about the degree of liner or coating wear or the location of wear in the pipe;
wherein identifiable compounds are encoded into different depth layers of the pipe liner or coating applied to an inner wall of the pipe, including where each layer is given a different combination, and including where each layer is poured and set, sprayed or cast depending on the manufacturing process; and
wherein the identifiable compounds comprise mix formulations of mineral elements that form part of an approach used to detect wear with a resolution via observation of an internal coating surface of the pipe, including using spectroscopic or analytical equipment and techniques.

38. Apparatus according to claim 37, wherein the apparatus comprises a pig or tractor configured to profile an entire pipeline, using a pig or tractor position to provide position, and a pigment ratio encoding to provide wear depth analysis.

39. Apparatus according to claim 38, wherein the apparatus comprises at least one beacon devices configured to provide external 'beacons' along the pipe, including an acoustic beacon, as at least one reference point for the pig or tractor to give accurate position determination.

40. Apparatus comprising:
a pipe configured to receive a process fluid flow; and
at least one pipe liner or coating configured to line or coat the pipe, configured with at least one chemical taggant or tracer, and configured to respond to the process fluid flow, and provide an indication about a degree of liner or coating wear or a location of wear in the pipe, based at least partly on the at least one chemical taggant or tracer,
wherein the at least one pipe liner or coating comprises at least one pigment; and
wherein the pipe liner or coating comprises modified mineral-loaded urethane coating layers, each modified mineral-loaded urethane coating layer configured with a different mineral.

41. Apparatus according to claim 40, wherein each modified mineral-loaded urethane coating layer is configured to indicate a percentage of wear, including about 0-25%, 25-50%, 50-75% and 75-100%.

42. Apparatus according to claim 41, wherein a first modified mineral-loaded urethane coating layer is configured to indicate a percentage of wear.

43. Apparatus according to claim 38, wherein the pig or tractor is configured to assess the 'mineral content of the coating, including using XRF or Raman analysis to map the wear along the entire pipeline.

44. A pipe comprising:
at least one pipe liner or coating configured to line or coat the pipe for receiving a process fluid flow therein, configured with at least one chemical taggant or tracer, and configured to respond to the process fluid flow, and provide an indication about a degree of wear or a location of wear in the pipe, the at least one pipe liner or coating comprising at least one embedded sensor element configured from the at least one chemical taggant or tracer and formed from a functionalized polymer, the at least one embedded sensor element being embedded in the pipe liner or coating, so that by tagging the pipe with different identifiers at different layers or levels within the pipe liner or coating, including with a "sub-tag", wear progression within specific sections or spools can be detected, determined and monitored, based at least partly on the at least one chemical taggant or tracer detected in the process flow.

45. A pipe according to claim 44, wherein the at least one embedded sensor element configured as a functionalized polymer sensor or a sensor made from the functionalized polymer.

46. A pipe according to claim 44, wherein the at least one pipe liner or coating comprises at least one pigment.

47. A method comprising:
configuring a pipe with at least one pipe liner or coating to line or coat the pipe for receiving a process fluid flow;
configuring the at least one pipe liner or coating with at least one chemical taggant or tracer; and
configuring the at least one pipe liner or coating to respond to the process fluid flow, and provide an indication about a degree of wear or a location of wear in the pipe;
wherein the method further comprises embedding in the at least one pipe liner or coating at least one sensor element configured from the at least one chemical taggant or tracer and formed from a functionalized polymer, so that by tagging the pipe with different identifiers at different layers or levels within the pipe liner or coating, including with a "sub-tag", wear progression within specific sections or spools can be detected, determined and monitored, based at least partly on the at least one chemical taggant or tracer detected in the process flow.

* * * * *